(12) United States Patent
Antonini

(10) Patent No.: US 7,935,821 B2
(45) Date of Patent: May 3, 2011

(54) METHOD FOR SEPARATION AND PURIFICATION OF NALTREXONE BY PREPARATIVE CHROMATOGRAPHY

(75) Inventor: Enrico A. Antonini, Edwardsville, IL (US)

(73) Assignee: Mallinckrodt Inc., Hazelwood, MO (US)

( * ) Notice: Subject to any disclaimer, the term of this patent is extended or adjusted under 35 U.S.C. 154(b) by 789 days.

(21) Appl. No.: 11/916,036

(22) PCT Filed: Jun. 7, 2006

(86) PCT No.: PCT/US2006/022196
§ 371 (c)(1), (2), (4) Date: Nov. 30, 2007

(87) PCT Pub. No.: WO2006/135650
PCT Pub. Date: Dec. 21, 2006

(65) Prior Publication Data
US 2010/0190986 A1      Jul. 29, 2010

Related U.S. Application Data

(60) Provisional application No. 60/688,956, filed on Jun. 9, 2005.

(51) Int. Cl.
*C07D 489/02* (2006.01)
*C07D 489/08* (2006.01)

(52) U.S. Cl. ............................................. 546/45; 546/44
(58) Field of Classification Search .................... 546/45, 546/44
See application file for complete search history.

(56) References Cited

U.S. PATENT DOCUMENTS

| 5,395,856 | A | 3/1995 | Haase |
| 5,578,725 | A | 11/1996 | Portoghese et al. |
| 5,600,809 | A | 2/1997 | Masui |
| 5,700,809 | A | 12/1997 | Leeson et al. |
| 6,359,111 | B1 | 3/2002 | Meyer et al. |
| 6,497,820 | B1 | 12/2002 | Goetzinger et al. |
| 6,500,840 | B2 | 12/2002 | Myers et al. |
| 2002/0132849 | A1 | 9/2002 | Hansen, Jr. et al. |
| 2004/0006114 | A1 | 1/2004 | Coleman et al. |
| 2005/0009860 | A1 | 1/2005 | Carson et al. |
| 2005/0014786 | A1 | 1/2005 | Sun et al. |

FOREIGN PATENT DOCUMENTS
WO      WO 03/074526      9/2003

OTHER PUBLICATIONS

Soni et al., "Separation of Standard Opiates and Their Analysis in Pharmaceutical and Illicit Preparations by Paired-In Reverse-Phase High-Pressure Liquid Chromatography", Journal of Forensic Sciences, vol. 24, 1979, pp. 437-447, XP008060065.
Kambia et al., "High-performance liquid chromatographic determination of naltrexone in plasma of hemodialysis patients", Biomedical Chromatography, 2000, 14(3), pp. 151-155, XP002401217.
Satyanarayana Valiveti et al., Development and validation of a liquid chromatography-mass spectrometry method for the quantitation of naltrexone and 6β-naltrexol in guinea pig plasma, Journal of Chromatography B, vol. 810, Issue 2, Oct. 25, 2004, pp. 259-267.
J. Alvarez-Fuentes et al., "Study of a complexation process between naltrexone and Eudragit® L as an oral controlled release system", International Journal of Pharmaceutics, vol. 148, Ussue 2, Mar. 28, 1997, pp. 219-230.
Davidson et al., "Determination of naltrexone and its major metabolite, 6-β-naltrexol, in human plasma using liquid chromatography with electrochemical detection", Journal of Pharmaceutical and Biomedical Analysis, vol. 14, Issue 12, Sep. 1996, pp. 1717-1725 (No title).
E.F. O'Connor et al., "Simultaneous extraction and chromatographic analysis of morphine, dilaudid, naltrexone and naloxone in biological fluids by high-performance liquid chromatography with electrochemical detection", Journal of chromatography B: Biomedical Sciences and Applications, vol. 491, 1989, pp. 240-247.
R. Ventura et al., "Analysis of naltrexone urinary metabolites", Journal of Pharmaceutical and Biomedical Analysis, vol. 6, Issues 6-8, 1988, pp. 887-893.

*Primary Examiner* — Charanjit S Aulakh

(57) ABSTRACT

A process for the purification of an impure preparation containing naltrexone by means of a reverse phase preparative chromatography process is provided. In an illustrative embodiment a chromatographic column is loaded with a stationary phase, typically a silica particle having an organic ligand bound thereto. With a loading ratio of from about 10 to about 1000 the impure preparation is acidified and passed through the column. The column is eluted with typically an aqueous solution with acetonitrile and the purified naltrexone is obtained in a specified fraction.

24 Claims, 2 Drawing Sheets

US 7,935,821 B2

METHOD FOR SEPARATION AND PURIFICATION OF NALTREXONE BY PREPARATIVE CHROMATOGRAPHY

CROSS REFERENCE TO RELATED APPLICATIONS

This application is a national stage application of PCT/US2006/022196, filed Jun. 7, 2006, which claims the benefit of U.S. Provisional Application No. 60/688,956 filed Jun. 9, 2005.

FIELD OF THE INVENTION

This invention relates to a method for the separation and purification of naltrexone by means of reverse phase preparative chromatography. More particularly, the process of this invention economically provides highly pure naltrexone in industrial quantities.

BACKGROUND OF THE INVENTION

Naltrexone is chemically 17-(cyclopropylmethyl)-4,5-epoxy-3, 14 dihydroxy-(5alpha)-morphinan-6-one, CAS RN 16590-41-3. Common trade names include Trexan® and Revia®. Naltrexone is an opioid antagonist with no agonist properties. It markedly blocks the physical dependence to opioids. Naltrexone is also used in reducing the craving for alcohol in treating alcoholism.

Methods for the synthesis of naltrexone have been described and are well known in the art. The overall molar yield of the conventional process from noroxymorphone to naltrexone hydrochloride has been reported to be about 65%. The overall yield to the anhydrous naltrexone base is typically about 45%. The levels of typical impurities, such as N-(3-butenyl)noroxymorphone (3BN) and 2,2-bisnaltrexone (2BN), need to be reduced to less than 0.50 area % to meet federal purity standards. There is therefore a need for a more efficient and direct method to isolate highly pure naltrexone, especially when producing industrial quantities.

Means to achieve separation or purification of pharmaceuticals include adsorption processes such as the use of carbon. Unfortunately, the carbon irreversibly adsorbs the pharmaceutical of interest in addition to removing color and other unwanted substances. This results in a significant yield loss.

In some instances, as in naltrexone, multiple precipitations are required in order to achieve the desired purity. This greatly reduces the overall yield when the supernatant streams are not recycled. These additional precipitations also require using a greater volume of naltrexone in the process with longer cycle times. Furthermore, the precipitation process can be lengthy in addition to the time that is sometimes required for heating and cooling. Moreover, some precipitations require extended filtration time due to the particle size of the product that is eventually produced.

Other drawbacks to the conventional process of purifying naltrexone include multiple manual solid handling operations to recover the naltrexone. These operations lead to greater operator exposure to the naltrexone with the associated reliance on engineering controls and personal protective equipment. This operation can be monotonous as well as tedious.

Another approach to purify naltrexone is the use of adsorption through ion exchange. Although this has been accomplished with alkaloids such as codeine and morphine, it has the limitation of requiring a low feed concentration. This is due to the need for the use of high pH flushes that can cause precipitation. Any precipitation can potentially compromise the entire ion-exchange resin column. Another disadvantage to this process is that due to the significant salt requirements, an additional step of dialysis or reverse osmosis is required for ion-removal.

Yet another process to achieve adsorption is through polar interaction or normal phase adsorption. Although this method can be successful, it requires extensive use of organic solvents. Moreover, although the naltrexone could be purified in this manner, more evaporation would be required.

Any use of analytical chromatography on naltrexone would guide an individual of ordinary skill in the art away from using preparative chromatography for an industrial scale process. Unlike preparative chromatography, analytical chromatography generally requires complete separation of each peak. The elution of the component peaks is measured often through the absorbance of ultraviolet (UV) light. In analytical chromatography the peak separation is achieved by loading an infinitely small mass of the feed onto the column, and using a small particle size diameter (often less than 5 micrometers in the stationary phase.) The small particle size generates much higher pressures than those found in preparative chromatography. These higher pressures mandate the use of very large, strong and expensive chromatography equipment, which would negate the commercial viability for this analytical process. The equipment would also be very large in consideration that an infinitely small mass of feed is loaded in each run. In preparative chromatography, the objective is to recover the desired feed component with the required purity. The desired component can be recovered with impurities, so long as the impurities are within specification limits. The particle size of the stationary phase is small enough to achieve the separation, but is often greater than 10 microns. This limits the pressure drop generated. Also, in preparative chromatography, the maximum amount of feed is loaded with the constraint of attaining the desired product quality. This allows the product to leave the column with a maximum concentration, which thereby minimizes the size of the downstream equipment, especially the evaporating or concentrating units.

The separation or purification of organics by means of chromatographic processes is well known in the art. However, the materials separated by means of the chromatographic processes are greatly dissimilar to the present objects of this invention, i.e. the industrial scale separation and purification of naltrexone. While there are numerous references to analytical chromatographic applications for naltrexone, there is no suggestion that an industrial process could be employed under previously known conditions.

The present invention is directed to overcoming one or more of the deficiencies set forth above. These deficiencies include, but are not limited to, product yield loss, tedious manual solid handling operations such as the loading and unloading of centrifuges or filters, reliance on protective equipment by the operator, extensive processing steps and multiple precipitations in order to achieve the requisite purity requirements.

SUMMARY OF THE INVENTION

In one aspect of the present invention there is provided a process for recovering highly pure naltrexone from an impure naltrexone preparation. The process comprises subjecting the impure naltrexone preparation to reverse-phase liquid chromatography wherein the loading ratio of a stationary phase to the naltrexone is not more than about 1000, and wherein the highly pure naltrexone recovered is at least about 95% pure.

In another aspect of the present invention there is provided a process for recovering highly pure naltrexone from an impure preparation. The process comprises subjecting the impure preparation to a reverse-phase high performance preparative liquid chromatography and recovering highly pure naltrexone.

In yet another aspect of the present invention there is provided a process for purifying an impure naltrexone preparation containing 3BN and 2BN. The process comprises the steps of packing a chromatographic column with a chromatographic packing material; passing an aqueous, acidified solution of naltrexone preparation through the column at a loading ratio of from about 10 to about 1000; and eluting the column with an aqueous solution to produce an eluate containing naltrexone having less than 0.50 area percent each of the 3BN and 2BN impurities.

DETAILED DESCRIPTION OF THE INVENTION

Figure 1:
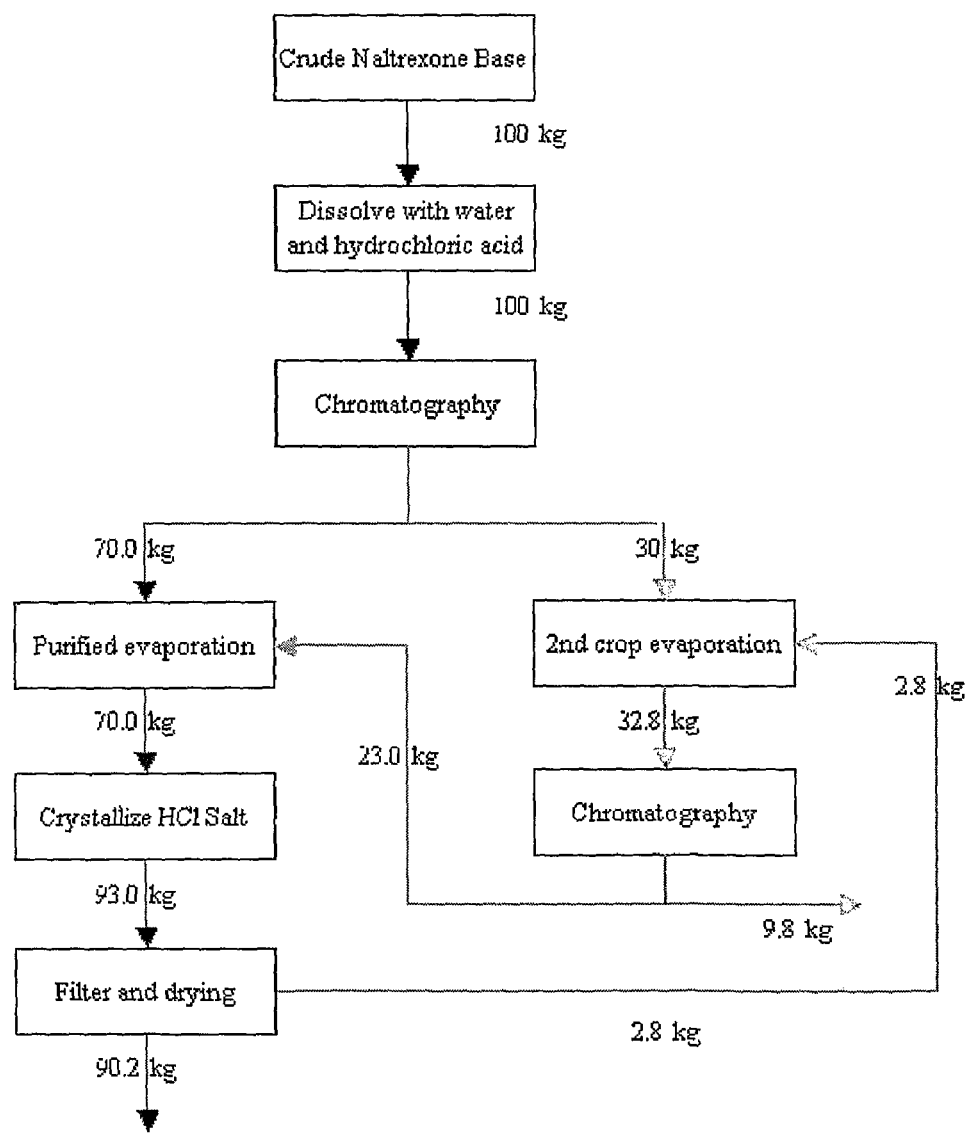
FIG. 1 is a flow chart of a non-limiting illustrative embodiment of the method of the present invention utilizing a crude naltrexone feed of 100 kg. In this figure the naltrexone product is the hydrochloride salt.

The process of the present invention is illustrated in FIG. 1. For purposes of this disclosure the following terms are defined:

Area %: A unit of purity calculated from analytical chromatography. It is the area of the desired component divided by the total area detected.

Loading ratio: Mass of stationary phase divided by the mass of alkaloid loaded in purification runs.

Mobile phase: The liquid that is pumped to the column after the feed is loaded. This liquid elutes the components.

Second crop: The alkaloid mass recovered in fractions that require a second pass through the chromatography column. The fractions are concentrated and then purified separately.

Stationary phase: The media that adsorbs the components of the feed to the column.

Yield: The mass of desired component recovered in purified fractions divided by the mass of component fed to the column.

Percent: Unless otherwise noted all percentage amounts stated in this specification and claims are percent by weight.

The production of naltrexone is initiated as in the conventional method. After synthesis, the naltrexone is extracted into an aqueous layer with hydrochloric acid. The aqueous layer is then treated with enough ammonium hydroxide to precipitate naltrexone alkaloid. The solids are isolated through centrifugation and dried.

At this point, rather than subject the solution to the alkaloid precipitation to form the second isolated base, the solids are dissolved with water and at least one acid, for example hydrochloric acid, to form the chromatography feed. The naltrexone is then purified through the chromatography column. The purified fractions are evaporated to attain the crystallization feed concentration. The concentrate is either cooled to form the purified naltrexone hydrochloride or treated with ammonium hydroxide to form the naltrexone base. In the case of the naltrexone base, the solids are then crystallized in methanol to form the anhydrous base product.

The mother liquor from either crystallization product is combined with the impure fractions from the chromatography. The naltrexone in the second crop composite is then concentrated through evaporation. The concentrate is then purified through the chromatography column and apart from any crude naltrexone base. No impure fractions are recycled in this purification, so that no impurities can accumulate. The purified naltrexone from the second crop is then combined with the purified material from the first crop in the evaporation step.

The proposed process will have a purification recovery of at least about 90%, preferably about 95% and an overall recovery of about 85% to produce the purified naltrexone salt. To produce the anhydrous naltrexone base, the proposed process with have a purification yield of at least about 80%, preferably about 88% and an overall recovery of about 80%. Using the chromatographic purification will reduce the 3BN and 2BN levels to less than 0.50 area percent.

In an alternative embodiment, the impure naltrexone preparation is acidified with an inorganic or organic acid to form a naltrexone salt prior to subjecting the impure naltrexone preparation to reverse-phase liquid chromatography. Suitable inorganic acids include sulfuric acid, hydrochloric acid, hydrobromic acid, phosphoric acid, phosphorous acid, nitric acid and mixtures thereof. Suitable organic acids include acetic acid, malic acid, tartaric acid, formic acid, oxalic acid, lactic acid and mixtures thereof. The resulting pH of the impure naltrexone preparation is typically about 1 to about 7, with a pH of about 2 to about 3 being preferred. The purification process for the naltrexone salt preparation proceeds as for the naltrexone preparation.

The stationary phase may be one of various materials from the group including but not limited to alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem, glycidoxyethylmethoxysilzne and mixtures thereof.

The stationary phase media utilized in an illustrative embodiment is silica with octadecyl-(C18) ligands, although other ligands such as octyl-(C8), butyl-(C4), tricosane-(C23) ligands, cyano or phenyl groups, as well as mixtures thereof, may be employed. The ligands can be attached to other particles such as polymers, zirconium oxide or titanium. The stationary phase is about 1 to about 200 microns, with about 15 to about 50 microns being preferred, and about 20 microns being most preferred. In this illustrative embodiment, spherical particles with pores of about 50 to about 300 Å are utilized, with about 90 to about 150 Å being preferred and about 120 Å being most preferred.

A high-performance preparative liquid chromatography column is generally employed. The preparative chromatography column, in an illustrative, non-limiting system, includes a diameter that is about 0.1 to about 200 cm with at least about 5 cm being preferred. The length of the preparative chromatography column is not critical to the process. A preferred length that ranges from about 10 centimeters to about 100 centimeters with a more preferred length that ranges from about 20 centimeters to about 30 centimeters, with about 25 centimeters in length being most preferred. There are a variety of commercial suppliers that can build preparative chromatography columns of this nature including Amicon, Inc., having a place of business at 72 Cherry Hill Drive, Beverly, Mass. 01915. Amicon, Inc. is the manufacturer of PROCHROM® chromatography columns. Other manufacturers include TechniKrom, Incorporated, having a place of business at 1801 Maple Avenue, Evanston, Ill. 60201. The present invention is applicable to a wide variety of high-performance liquid preparative chromatography columns and is not limited to the specific embodiment detailed in this patent application.

Naltrexone and its impurities are adsorbed onto the stationary phase and are desorbed, or eluted with a mobile phase containing at least one dilute acid and at least one organic polar solvent. Suitable acids include but are not limited to acetic acid, formic acid, oxalic acid, lactic acid, malic acid, sulfuric acid, hydrochloric acid, hydrobromic acid, phosphoric acid, phosphorous acid, nitric acid and mixtures thereof, with hydrochloric acid being preferred. The organic polar solvent is selected from any number of water soluble, non-interfering solvents such as alcohols, including ethanol, methanol, propanol, isopropanol, butanol, t-butanol and mixtures thereof, as well as acetonitrile. The aqueous mobile phase is prepared by acidifying the water to attain a pH of about 1 to about 7, with a more preferred pH range of about 3.5 to about 5.5. Typically, the amount of organic solvent in the mobile phase increases during the elution process. Lower amounts of organic solvent are used in the first few passes of mobile phase through the column, with increasing amounts employed in later passes in order to purge the column.

A critical feature of this invention is the Loading Ratio. It has been found that the Loading Ratio employed in the process of this invention is typically in the range of from about 10 to about 1000 grams of media per gram of naltrexone loaded into the column before the mobile phase is employed. In a preferred illustrative embodiment, the Loading Ratio is in the range of from about 20 to about 40. As is well known, in the analytical use of HPLC the Loading Ratio would be above 10,000 and the feed components would elute in separate peaks. In the preparative chromatography such Loading Ratio would multiply the number of runs in a column by a factor of over 500 or cause the column to be more than 20 times larger diameter. Using the analytical loading conditions would make any new chromatography purification technique impractical, especially at industrial quantities. The preparative application of the present invention has elution fronts, in which the naltrexone is collected with the desired purity.

The desired purity obtained in the process of this invention is, of course, in some measure dependent upon the amount of impurities and operating conditions of the chromatographic process. In instances of higher impurities, a Loading Ratio in the higher level of the above noted preferred range would be required. Also, the amount of organic solvent in the mobile phase must be controlled so as not to elute impurities prematurely. As can be seen in the operating examples below those runs with a higher total amount of elution produced higher impurities.

In operation, after the naltrexone feed solution is loaded into the packed column, the first components are eluted with a mobile phase containing no organic solvent. Some of the impurities are collected in a first fraction that is discarded. A second fraction is collected containing an initial, small amount of naltrexone and impurities. The second fraction will contain about 5 percent of the naltrexone loaded. The purified naltrexone is then collected in the third fraction wherein the mobile phase remains completely aqueous. The third fraction contains about 80 percent of the naltrexone loaded onto the column. This third fraction is evaporated to remove most of the water and the purified naltrexone is recovered from solution by precipitation in accordance with standard procedures. The fourth fraction will collect most of the remaining naltrexone, typically about 15 percent, in a flush containing about 50% to about 80% organic solvent. In this illustrative embodiment, the preferred solvent is acetonitrile. A fifth fraction is then obtained to flush the column of the remaining impurities. In the fifth fraction, the mobile phase employed contains about 80% to about 100% organic solvent, typically acetonitrile.

The fourth fraction is then combined with the second fraction and subjected to evaporation to remove the organic solvent. The combined fractions are subjected to the preparative, reverse phase preparative chromatography as described above except that no recycle fractions are collected in order to purge the impurities. The purified, combined second crop is then sent to the precipitation procedure as noted above with respect to the third fraction.

The reverse phase, preparative chromatographic process of this invention is typically operated at a temperature of from about 10° C. to about 50° C., with about 20° C. to about 30° C. being preferred. It is noted however that temperature is not critical in this process. Higher or lower temperatures may be employed without significant change in result.

Figure 2:
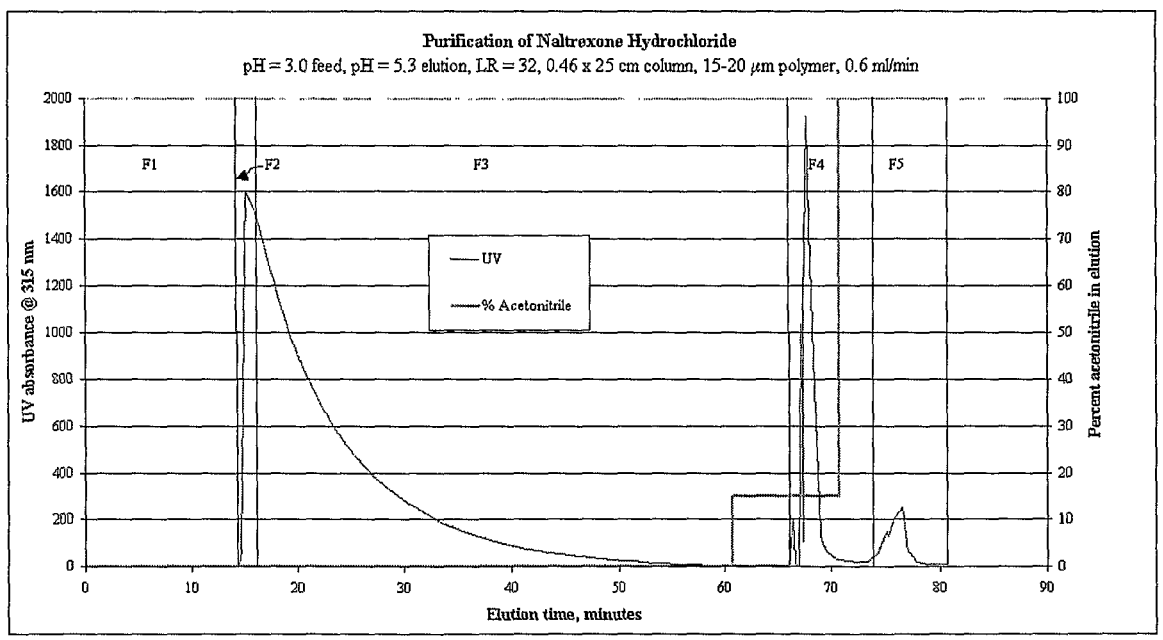
FIG. 2 is a graph indicating the results of a non-limiting illustrative embodiment of a reverse phase, preparative HPLC procedure in accordance with this invention wherein the UV analysis of the product provides an indication of the contents of each fraction of eluant delivered from the column. The Figure also indicates the time; fraction cut lines of each of four fractions and the acetonitrile content of the mobile phase employed in the process.

In operation, it is typical to employ UV analysis of the eluted material from the column. A typical UV profile of eluted material in accordance with the process of this invention appears in FIG. 2. The process producing the UV curve in FIG. 2 employed a feed solution of naltrexone hydrochloride salt at pH 3.0 to a chromatographic column having a dimension of 0.46×25-cm, with 20 micron polymeric particles. The Load Ratio was 30 and the flow rate was 0.65 ml/min. In the Figure, the abscissa denotes elution time in minutes while the left ordinate denotes UV absorbance at 310 nm. The right ordinate denotes percent acetonitrile in volume percent in the feed solution. The various fractions collected are denoted as F1-F5.

EXAMPLES

Example 1

Two chromatographic runs were made employing the following conditions:

Objective: Recover naltrexone with less than 0.50 area percent 3BN and 2BN.

Feed Composition: 95.82 area % naltrexone, 0.44 area % 3BN and 0.81 area % 2BN

Feed pH: 3.00 with hydrochloric acid

Feed concentration: 28-g/l naltrexone

Stationary phase: 20-micron hydrophobic polymeric spherical particles with 120-angstrom pores.

Column: 0.46-cm diameter, 25-cm length, and 2.2 g of stationary phase

Flow Rate: 0.64 ml/min.

Flow direction: top to bottom

Temperature: 26° C.

Detection: 315 nm.

Mobile Phase: dilute hydrochloric acid solution in water and acetonitrile (ACN) added in step gradients of 50 to 100 volume percent.

The results of the first and second trials appear in Table I below. This was a comparison of the effect of the feed loading.

TABLE I

|  | Trial 1 | Trial 2 |
| --- | --- | --- |
| Loading Ratio | 32 | 14 |
| Mobile phase pH | 5.26 | 3.96 |
| Area % naltrexone in purified fraction | 99.82 | 98.93 |
| Area % of 3BN in purified fraction | 0.00 | 0.23 |
| Area % of 2BN in purified fraction | 0.16 | 0.42 |
| Yield of naltrexone in purified fraction | 78 | 72 |
| Elution of fraction F1 | 8.4 ml of aqueous | 7.8 ml of aqueous |
| Elution of second crop fraction F2 | 1.1 ml of aqueous | 2.3 ml of aqueous |
| Elution of purified fraction F3 | 32.2 ml of aqueous | 25.6 ml of aqueous |
| Elution of second crop fraction F4 | 5.4 ml of 75% ACN | 6.4 ml of aqueous<br>5.7 ml of 50% ACN |
| Elution of fraction F5 | 4.3 ml of 100% ACN | 4.6 ml of 100% ACN |

In Trial 1 the naltrexone was purified to 99.82 area % with no 3BN detected and 0.16 area % 2BN. Trial 1 used a loading ratio of 32 g media/g naltrexone, while Trial 2 loaded too much feed at a ratio of 14. Trial 1 was able to recover 78% of the naltrexone in the purified F3 fraction, while Trial 2 recovered less at 72% due to greater impurity elution. More impurity elution occurred with the naltrexone with more feed loaded on the column. The remaining naltrexone yield was recovered in Fractions F2 and F4 in both trials. These fractions were designated as second crop and were to be purified a second time through the column.

Example 2

Objective: Recover naltrexone with less than 0.50 area percent 3BN and 2BN.

Feed composition: 95.82 area % naltrexone, 0.44 area % 3BN and 0.81 area % 2BN

Feed concentration: 28 g/l naltrexone in aqueous solution

Stationary phase: silica with C18 ligands, 20 μm spherical particles with 120 Å pores.

Column: 1.0 cm diameter, 25 cm length, 10.2 g of stationary phase

Flow Rate: 3 ml/min

Flow direction: top to bottom

Temperature: 27° C.

Detection: 315 nm

Mobile phase: dilute hydrochloric acid solution in water and ACN. The acetonitrile is added in step gradients of 10-100 volume percent Another pair of trials was made to compare the effect of the mobile phase pH. The results of the runs are contained in Table II below.

In Table II Trial 3 used a feed and mobile phase pH both above 5. This trial sufficiently reduced all impurities, and 92% of the naltrexone was recovered in the purified fraction F3. Trial 4 used lower feed and mobile phase pH both below 3. This caused a more rapid elution of the naltrexone and impurities. No F2 second crop fraction could be collected in Trial 4 due to a significant initial elution of naltrexone with impurities. Although the overall purity of naltrexone was greater in Trial 4 at 99.55 area %, it had a larger content of the 3BN impurity. Other trials showed that the reduction of 3BN was improved with mobile phase pH above 3.5. The more gradual elution of Trial 3 allowed for a greater recovery of naltrexone before the late-running impurities eluted.

Example 3

Trials 5 and 6, given in Table III below compare the selection of the media for separation.

Objective: Recover naltrexone with less than 0.50 area percent 3BN and 2BN.

Feed composition: 95.82 area % naltrexone, 0.44 area % 3BN and 0.81 area % 2BN

Feed concentration: 28 g/l naltrexone in aqueous solution

Feed pH: 2.24 with hydrochloric acid

Stationary phase: 20 μm spherical particles with 120 Å pores.

Column: 1.0 cm diameter, 25 cm length, 10.2 g of stationary phase

Flow Rate: 3 ml/min

Flow direction: top to bottom

Temperature: 27° C.

Detection: 315 nm

Mobile phase: dilute hydrochloric acid solution in water at pH=2.74 and acetonitrile (ACN). The acetonitrile is added in step gradients of 7-100 volume percent

TABLE II

|  | Trial 3 | Trial 4 |
| --- | --- | --- |
| Loading Ratio | 38 | 31 |
| Feed pH | 5.57 | 2.24 |
| Mobile phase pH | 5.26 | 2.74 |
| Area % naltrexone in purified fraction | 99.43 | 99.55 |
| Area % of 3BN in purified fraction | 0.20 | 0.32 |
| Area % of 2BN in purified fraction | 0.14 | 0.07 |
| Yield of naltrexone in purified fraction | 92 | 86 |
| Elution of fraction F1 | 44.5 ml of aqueous | 41 ml of aqueous |
| Elution of second crop fraction F2 | 4.4 ml of aqueous | Not taken |
| Elution of purified fraction F3 | 96.5 ml of aqueous | 87.2 ml of aqueous |
| Elution of second crop fraction F4 | 11.4 ml of 15% ACN<br>20.9 ml of 60% ACN | 30.0 ml of 10% ACN |
| Elution of fraction F5 | 36.0 ml of 100% ACN | 31.5 ml of 70% ACN |

TABLE III

|  | Trial 5 | Trial 6 |
| --- | --- | --- |
| Stationary phase | C18 silica | C4 silica |
| Loading Ratio | 61 | 64 |
| Area % naltrexone in purified fraction | 99.77 | 99.07 |
| Area % of 3BN in purified fraction | 0.23 | 0.31 |
| Area % of 2BN in purified fraction | 0.00 | 0.05 |
| Area % of noroxymorphone in purified fraction | 0.00 | 0.47 |
| Yield of naltrexone in purified fraction | 80 | 93 |
| Elution of fraction F1 | 59.4 ml of aqueous | 18.2 ml of aqueous |
| Elution of second crop fraction F2 | Not taken | Not taken |
| Elution of purified fraction F3 | 85.2 ml of aqueous | 54.6 ml of aqueous |
| Elution of second crop fraction F4 | 32.5 ml of 15% ACN | 29.0 ml of 7% ACN |
| Elution of fraction F5 | 31.5 ml of 100% ACN | 30.0 ml of 60% ACN |

Trial 5 used the C18 silica and it was able to purify the naltrexone to 99.77 area % purity with 0.23 area % 3BN. Trial 6 used the C4 silica, which eluted the naltrexone with 99.07 area % purity and significant levels of 3BN and noroxymorphone. Both trials were run at the same loading ratio and mobile phase pH. The C4 silica allowed for a quicker arrival of the naltrexone and a greater recovery in the F3 fraction. Unfortunately, the C4 silica was unable to separate away the impurities sufficiently. The C4 silica could be used if better fraction collection were used, in which more naltrexone is collected in the second crop fractions to improve purity.

There has been described a novel process for naltrexone purification by means of reverse phase, preparative chromatography. While the process of this invention has been described with reference to specific compounds and examples, no intention is made by such reference to limit the scope of this invention unless expressly stated. Various modifications may be made in the materials and sequence of process steps as well as process combinations, which are adapted to suit the various process steps without departing from this invention. The foregoing description is given for clarity of understanding only and no unnecessary limitations should be understood there from, as modifications will be obvious to those skilled in the art.

What is claimed is:

1. A process for recovering highly pure naltrexone from an impure naltrexone preparation, the process comprising:
   loading the impure naltrexone preparation into a reverse-phase preparative chromatographic column, wherein the loading ratio of a stationary phase to naltrexone is not more than about 1000; and
   recovering highly pure naltrexone by eluting the naltrexone from the reverse-phase preparative chromatographic column with a mobile phase, wherein the highly pure naltrexone recovered is at least about 95% pure.

2. The process of claim 1 wherein the loading ratio is in the range of about 10 to about 1000.

3. The process of claim 1 wherein the loading ratio is in the range of about 20 to about 40.

4. The process of claim 1 wherein the stationary phase is selected from the group consisting of alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem, glycidoxyethylmethoxysilzne and mixtures thereof.

5. The process of claim 1 wherein the stationary phase is a bonded-phase silica containing ligands selected from the group consisting of butyl-, octyl-, octadecyl-, tricosane-, cyano- and phenyl-moieties, and mixtures thereof.

6. The process of claim 5 wherein the ligand is octadecylsilane.

7. The process of claim 1 wherein the mobile phase comprises water, acid and an organic solvent.

8. The process of claim 7 wherein the acid in the mobile phase is selected from the group consisting of acetic acid, malic acid, tartaric acid, sulfuric acid, formic acid, oxalic acid, lactic acid, hydrochloric acid, hydrobromic acid, phosphoric acid, phosphorous acid, nitric acid and mixtures thereof.

9. The process of claim 8 wherein the pH of the mobile phase is about 1 to about 7.

10. The process of claim 9 wherein the pH of the mobile phase is about 3.5 to about 5.5.

11. The process of claim 7 wherein the organic solvent includes at least one alcohol.

12. The process of claim 11 wherein the at least one alcohol is selected from the group consisting of methanol, propanol, isopropanol, butanol, butanol and mixtures thereof.

13. The process of claim 7 wherein the organic solvent includes acetonitrile.

14. The process of claim 13 wherein the acetonitrile is about 5 to about 100 volume percent.

15. The process of claim 13 where the acetonitrile is up to 10 volume percent during the recovery of the purified naltrexone.

16. The process of claim 1 further comprising acidifying the impure naltrexone preparation to form a naltrexone salt prior to subjecting the impure naltrexone preparation to reverse-phase liquid chromatography.

17. The process of claim 16 wherein the impure naltrexone preparation is acidified with at least one inorganic acid.

18. The process of claim 17 wherein the at least one inorganic acid is selected from the group consisting of sulfuric acid, hydrochloric acid, hydrobromic acid, phosphoric acid, phosphorous acid, nitric acid and mixtures thereof.

19. The process of claim 16 wherein the impure naltrexone preparation is acidified with at least one organic acid.

20. The process of claim 19 wherein the organic acid is selected from the group consisting of acetic acid, malic acid, tartaric acid, formic acid, oxalic acid, lactic acid and mixtures thereof.

21. The process of claim 16 wherein the pH of the impure naltrexone preparation is about 1 to about 7.

22. The process of claim 21 wherein the pH of the impure naltrexone preparation is about 2 to about 3.

23. A process for purifying an impure naltrexone preparation containing 2,2-bisnaltrexone and N-(3-butenyl)noroxymorphone, the process comprising the steps of
(a) packing a preparative chromatographic column with a chromatographic packing material;
(b) passing through the packed, preparative chromatographic column an aqueous, acidified solution of naltrexone preparation at a loading ratio of from about 10 to about 1000; and
(c) eluting naltrexone from the packed chromatographic column with a mobile phase comprising water and an organic solvent to produce an eluate containing a purified naltrexone with less than 0.50 area % 2,2-bisnaltrexone and less than 0.50 area % N-(3-butenyl)noroxymorphone.

24. The process of claim 23 further including dividing the eluate into at least four fractions wherein:
(i.) a first fraction is discarded,
(ii.) a second fraction is combined with a fourth fraction wherein the water and organic solvent are substantially reduced and then recycled through the column, and
(iii.) a third fraction that contains less than 0.50 area % 2,2-bisnaltrexone and N-(3-butenyl)noroxymorphone is recovered.

* * * * *